United States Patent [19]

Sugimori et al.

[11] Patent Number: 4,654,162

[45] Date of Patent: Mar. 31, 1987

[54] ALCOHOL DERIVATIVES

[75] Inventors: Shigeru Sugimori, Fujisawashi; Yasuyuki Goto, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 764,781

[22] Filed: Aug. 12, 1985

[30] Foreign Application Priority Data

Aug. 13, 1984 [JP] Japan .................................. 59-168941
Sep. 12, 1984 [JP] Japan .................................. 59-191192

[51] Int. Cl.⁴ ...................... C09K 19/30; C09K 19/54; C07C 41/00; C07C 43/02; C07C 43/20; C07C 121/60

[52] U.S. Cl. ........................ 252/299.63; 252/299.01; 252/299.5; 252/299.66; 568/642; 568/643; 568/644; 568/631; 558/423; 350/350 R; 350/350 S

[58] Field of Search ....................... 252/299.01, 299.63, 252/299.5, 299.66; 260/465 F; 568/642, 643, 644, 631; 558/423; 350/350 R, 350 S

[56] References Cited

U.S. PATENT DOCUMENTS

| | | | |
|---|---|---|---|
| 2,789,965 | 4/1957 | Reynolds et al. | |
| 3,947,375 | 3/1976 | Gray et al. | 252/299.66 |
| 4,130,502 | 12/1978 | Eidenschink et al. | 252/299.63 |
| 4,180,475 | 12/1979 | Schadt et al. | 252/299.5 |
| 4,293,435 | 10/1981 | Portugall et al. | 252/299.01 |
| 4,374,748 | 2/1983 | Imufai et al. | 252/299.66 |
| 4,468,340 | 8/1984 | Inoue et al. | 252/299.63 |
| 4,556,727 | 12/1985 | Walba | 252/299.67 |
| 4,564,694 | 1/1986 | Hirai et al. | 252/299.63 |

FOREIGN PATENT DOCUMENTS

| | | | |
|---|---|---|---|
| 2636684 | 2/1978 | Fed. Rep. of Germany | 252/299.63 |
| 2917131 | 11/1979 | Fed. Rep. of Germany . | |
| 56-36568 | 4/1981 | Japan | 252/299.66 |
| 57-34176 | 2/1982 | Japan | 252/299.63 |
| 57-99542 | 6/1982 | Japan | 252/299.63 |
| 57-162773 | 10/1982 | Japan | 252/299.63 |
| 58-167671 | 10/1983 | Japan | 252/299.63 |

OTHER PUBLICATIONS

Shibaev, V. P., et al., Eur. Polym. J., vol. 18(8), pp. 651-659 (1982).
Demus, D., Nonemissive Electrooptic Displays, pp. 83-119 (1975).
Finkelmann, H., et al., Liquid Crystal Polymers II/III, Ed. Gordon, M., et al., Springer-Verlag, Berlin, pp. 99-101, 106, 114-115, 146, 147, 168-172 (1984).
Shibaev, V., et al., Liquid Crystal Polymers II/III, Ed. Gordon, M., Springer-Verlag, Berlin, pp. 173-252 (1984).
C.A. 98, 54755s (1983).

Primary Examiner—Teddy S. Gron
Attorney, Agent, or Firm—Wenderoth, Lind & Ponack

[57] ABSTRACT

A novel compound usable as a component constituting liquid crystal materials having a positive dielectric anisotropy value and a liquid crystal composition containing the same are provided, which compound is an alcohol derivative expressed by the general formula

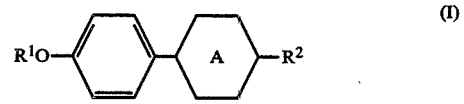

wherein $R^1$ represents a hydroxyalkyl group of 1 to 10 carbon atoms having hydroxyl group at the end or an intermediate position thereof; $R^2$ represents an alkyl group or an alkoxy group each of 1 to 10 carbon atoms or $-C\equiv N$; and

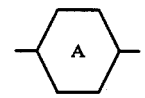

represents

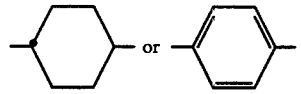

and when $R^2$ represents $-C\equiv N$,

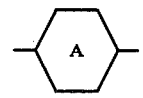

represents

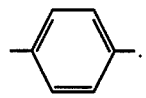

2 Claims, No Drawings

ALCOHOL DERIVATIVES

BACKGROUND OF THE INVENTION

1. Field of the Invention

This invention relates to a novel organic compound and more particularly it relates to a novel organic compound capable of being used as a component constituting liquid crystal materials having a positive dielectric anisotropy value.

2. Description of the Prior Art

Liquid crystal display elements utilize the optical anisotropy and dielectric anisotropy of liquid crystal substances. Their display modes include various ones such as TN type (twisted nematic type), DS type (dynamic scattering type), guest-host type, DAP type, White-Tailor type, etc. and the properties required for liquid crystal substances used vary depending on the respective modes. For example, depending on the kinds of display elements, liquid crystal substances having a positive dielectric anisotropy value Δε are required, those having a negative one are required or those having an intermediate value therebetween are suitable. Further, it is necessary for liquid crystal substances used to exhibit a liquid crystal phase within a temperature range which is as broad as possible, and to be stable to moisture, heat, air, light, etc. At present, however, there is no single substance which satisfies all of such conditions, but several kinds of liquid crystal substances are mixed with one another or with non-liquid crystal substances, for practical use.

European patent application publication No. 0058981 A2 discloses the following compounds:

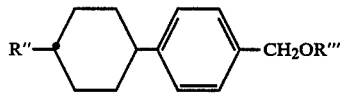

(A)

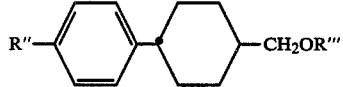

(B)

and

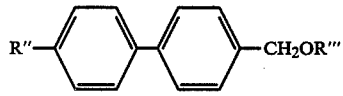

(C)

wherein R'' and R''' each represent an alkyl group of 1~12 carbon atoms.

The compounds (A), (B) and (C), however, have a drawback that they have a low nematic-clearing point so that the mesomorphic range of the resulting liquid crystal composition is narrowed; hence they are unsuitable for use as a component constituting liquid crystal compositions.

SUMMARY OF THE INVENTION

A first object of the present invention is to provide a novel organic compound suitable for use as a component constituting liquid crystal composition, and a second object of the present invention is to provide a liquid crystal composition for use as a material for liquid crystal display devices which are operated under low driving voltages. These objects are achieved by a compound and a liquid crystal composition described below.

The present invention in a first aspect resides in the following main constitution (1) and constitutions (2)~(4) as its preferable embodiments:

(1) an alcohol derivative expressed by the general formula

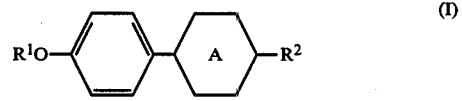

(I)

wherein $R^1$ represents a hydroxyalkyl group of 1 to 10 carbon atoms having hydroxyl group at the end or an intermediate position thereof; $R^2$ represents an alkyl group or an alkoxy group each of 1 to 10 carbon atoms or —C≡N; and

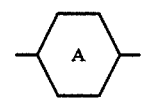

represents

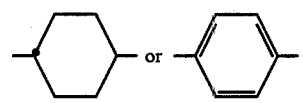

and when $R^2$ represents —C≡N,

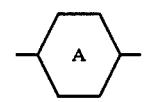

represents

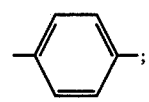

;

(2) a 4-cyano-4'-(hydroxyalkoxy)biphenyl according to the above item (1) wherein said

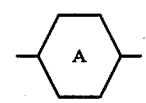

represents

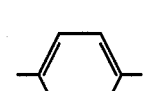

and $R^2$ represents —C≡N;

(3) a 1-hydroxyalkoxy-4-(trans-4-alkylcyclohexyl)-benzene according to the above item (1) wherein said represents

and (4) a 4-alkyl-4'-(hydroxyalkoxy)biphenyl according to the above item (1) wherein said

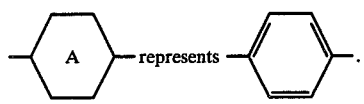

The present invention in a second aspect resides in (5) a liquid crystal composition having at least two components at least one of which is a compound set forth in the above item (1).

DETAILED DESCRIPTION OF THE PREFERRED EMBODIMENTS

Preparation of the compounds of the present invention will be described below.

A 4-substituted-phenol (III) is reacted with a brominated alcohol derivative (II) (the alkyl group forming the alcohol being the same as the alkyl group of the above hydroxyalkyl group) in ethyl alcohol in the presence of potassium hydroxide or sodium hydroxide to obtain a 1-(4-hydroxyalkoxy)-4-substituted benzene(I) as a compound of the present invention. This reaction will be shown by the following chemical equation:

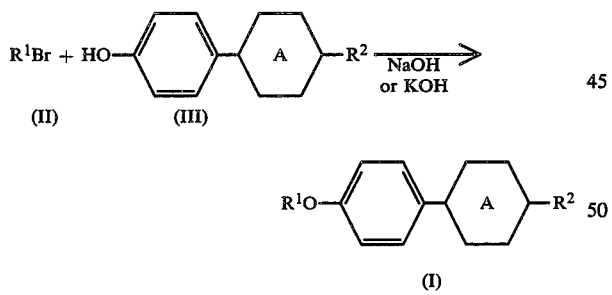

wherein $R^1$, $R^2$ and

each are as defined above.

Among the compounds of the present invention, many of those having a branched carbon chain as $R^1$ or $R^2$ generally per se exhibit no liquid crystal phase but they have a good compatibility with other liquid crystal compounds and hence are useful as a component constituting liquid crystal compositions. However, they often reduce the nematic-isotropic liquid phase transition point of liquid crystal compositions using them; hence in order to effect a broad liquid crystal phase temperature range, $R^1$ and $R^2$ each are preferred to be a linear carbon chain.

The compounds of the present invention have a superior compatibility with other liquid crystal compounds, exhibit a positive dielectric anisotropy value and can reduce the driving voltage of liquid crystal compositions having the compounds added as a component, as shown in Examples mentioned later.

The liquid crystal compositions of the present invention contain the compounds of the present invention expressed by the formula (I) preferably in a quantity of 1 to 30% by weight, and more preferably in 5 to 20% by weight. If the content of the compounds of the formula (I) therein is less than 1% by weight, contribution of the compositions to reduction in the driving voltage of the compositions is small, while if the content exceeds 30% by weight, the viscosity of the compositions increases and hence such an excess content is not practical.

Existing liquid crystal compounds usable for the liquid crystal compositions of the present invention may be choiced from compounds belonging to groups expressed by the following general formulas (i)~(xxxii), wherein X represents

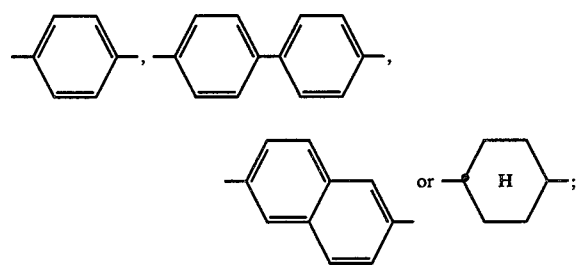

Y represents —CN, $R^1$ or halogen; and R and $R^1$ each represent an alkyl group:

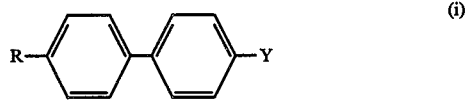
(i)

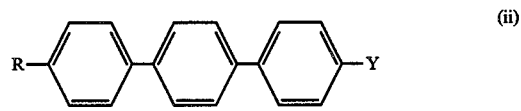
(ii)

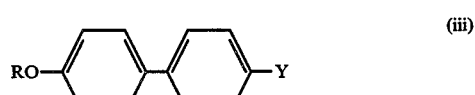
(iii)

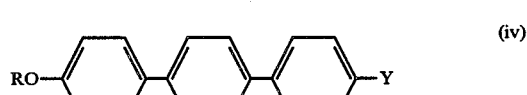
(iv)

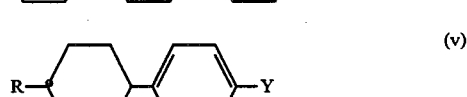
(v)

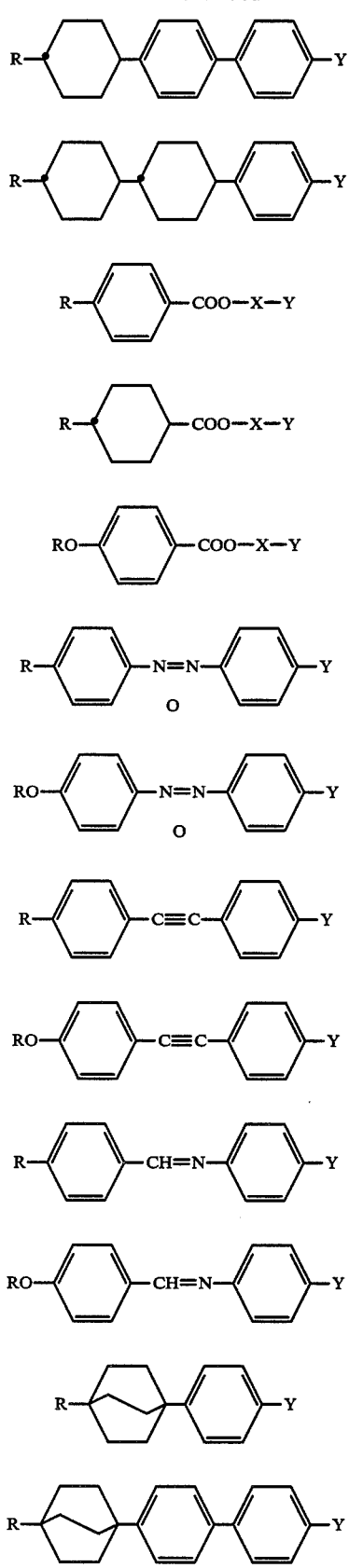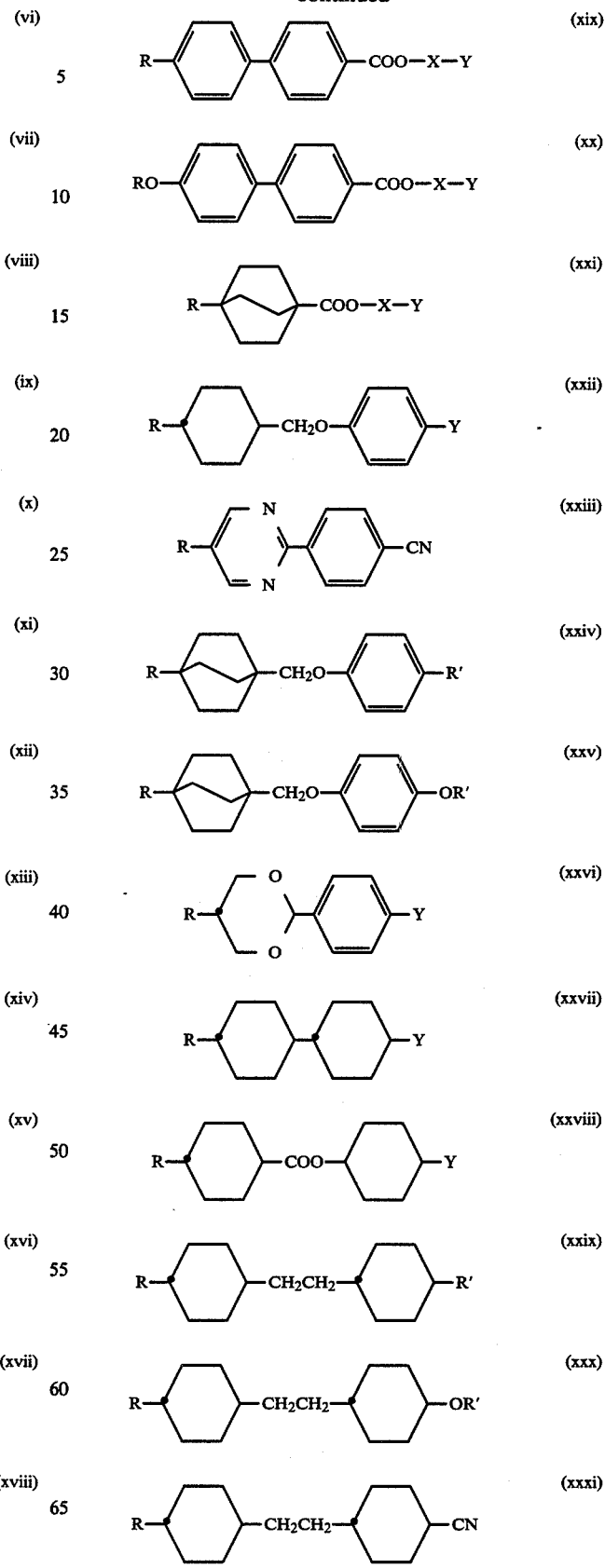

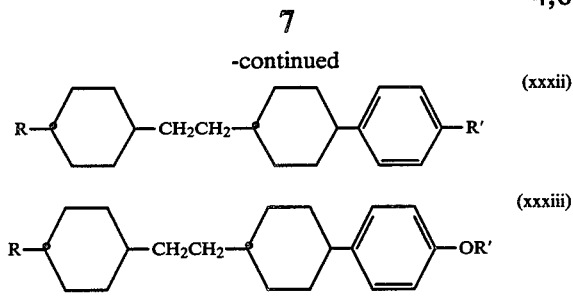

The present invention will be described below in more detail by way of Examples, but it should not be construed to be restricted thereto.

The following symbols are employed in the respective Examples:
- C-S: crystalline-smectic phase transition point
- S-N: smectic-nematic phase transition point
- C-N: crystalline-nematic phase transition point
- N-I: nematic-isotropic liquid phase transition point
- C-I: crystalline-isotropic liquid phase transition point
- S-I: smectic-isotropic liquid phase transition point

EXAMPLE 1

4-Cyano-4'-(3-hydroxypropoxy)biphenyl

3-Bromo-1-propanol (5.6 g, 0.04 mol) and 4-cyano-4'-hydroxybiphenyl (6.0 g, 0.02 mol) were dissolved in ethanol (300 ml) and agitated at room temperature. To this solution was gradually dropwise added a solution of KOH (10 g) dissolved in water (20 ml), over 30 minutes, followed by stirring for 40 hours, distilling off about 200 ml of ethanol under reduced pressure, adding water (500 ml) to deposit solids, adding toluene (300 ml) to the mixture system, filtering off insoluble matter, washing the toluene solution twice with 2N-NaOH, then three times with water, drying over anhydrous sodium sulfate, distilling off toluene, and recrystallizing the resulting crystals from methanol to obtain 4-cyano-4'-(3-hydroxypropoxy)biphenyl. Yield: 2 g (28%). C-N: 109.0°–110.7° C. N-I: 113.6° C.

EXAMPLE 2

1-(2-Hydroxyethoxy)-4-(trans-4-propylcyclohexyl)benzene

2-Bromo-1-ethanol (5.0 g, 0.04 mol) and 4-(trans-4-propylcyclohexyl)phenol (4.4 g, 0.02 mol) were dissolved in ethanol (300 ml) and agitated at room temperature. To this solution was gradually dropwise added a solution of KOH (10 g) in water (20 ml), over 30 minutes, followed by stirring for 40 hours, distilling off about 200 ml of ethanol under reduced pressure, adding water (500 ml) to deposit solids, separating the solids from liquid, dissolving them in toluene (100 ml), filtering off insoluble matter, washing the toluene solution twice with 2N-NaOH, then three times with water, drying over anhydrous sodium sulfate, distilling off toluene and recrystallizing the resulting crystals from n-heptane to obtain the objective 1-(2-hydroxyethoxy)-4-(trans-4-propylcyclohexyl)benzene. Yield: 1.8 g (34%). C-S: 71.5° C. S-I: 81.4° C.

EXAMPLES 3–11

The following compounds were obtained in the same manner as in Examples 1 and 2:

4-cyano-4'-(2-hydroxyethoxy)biphenyl
 C-I: 124.0°–126.9° C., N-I: 122.5° C.
4-cyano-4'-(2-hydroxypropxy)biphenyl
 C-I: 111.9°–113.8° C., N-I: 79.4° C.
1-(3-hydroxypropoxy)-4-(trans-4-propylcyclohexyl)benzene
 C-S: 65.8° C., S-I: 77.8° C.
1-(2-hydroxypropoxy)-4-(trans-4-propylcyclohexyl)benzene
 C-I: 86.3°–90.7° C.
1-(2-hydroxyethoxy)-4-(trans-4-ethylcyclohexyl)benzene
 C-I: 82.0°–85.7° C., S-I: 61.1° C.
1-(3-hydroxypropoxy)-4-(trans-4-methylcyclohexyl)benzene
 C-I: 69.2°–70.5° C., S-I: 33.3° C.
4-(2-hydroxyethoxy)-4'-pentylbiphenyl
 C-I: 134.3°–135.0° C.
4-(3-hydroxypropoxy)-4'-pentylbiphenyl
 C-I: 123.8°–125.5° C.

EXAMPLE 12

A liquid crystal composition (A) consisting of
trans-4-propyl-(4'-cyanophenyl)cyclohexane
 28% by weight,
trans-4-pentyl-(4'-cyanophenyl)cyclohexane
 42% by weight and
trans-4-heptyl-(4'-cyanophenyl)cyclohexane
 30% by weight,
has a N-I point of 52° C., a dielectric anisotropy value of 11.2 and a viscosity at 20° C. of 23 cp. A liquid crystal cell obtained by filling the above composition (A) in a TN cell having therein opposed transparent electrodes having a space of 10 μm therebetween exhibits a threshold voltage of 1.54 V and a saturation voltage of 2.12 V.

A liquid crystal composition consisting of the above liquid crystal composition (A) (90 parts by weight) and 4-cyano-4'-(3-hydroxypropoxy)biphenyl (10 parts by weight) of the present invention obtained in Example 1 had a N-I point of 56° C., a dielectric anisotropy value of +14.6 and a viscosity at 20° C. of 36 cp. A liquid crystal cell obtained by filling this composition in the above TN cell exhibited a threshold voltage of 1.34 V and a saturation voltage of 1.85 V.

EXAMPLE 13

A liquid crystal composition (B) consisting of
trans-4-propyl-(4'-cyanophenyl)cyclohexane
 24% by weight,
trans-4-pentyl-(4'-cyanophenyl)cyclohexane
 36% by weight,
trans-4-heptyl-(4'-cyanophenyl)cyclohexane
 25% by weight and
trans-4-pentyl-(4-cyanobiphenyl)cyclohexane
 15% by weight, has a nematic-clearing point of 72.0° C., a dielectric anisotropy value of +11.6 and a viscosity at 20° C. of 27.8 cp. A liquid crystal cell obtained by filling the liquid crystal composition (B) in a TN cell composed of two opposed substrates each having a transparent electrode of tin oxide coated with silicon oxide and subjected to rubbing treatment, and having a space between the electrodes of 10 μm was subjected to measurement of its specific features at 20° C. The cell exhibited a threshold voltage of 1.75 V and a saturation voltage of 2.40 V.

A liquid crystal composition (C) obtained by blending 1-(3-hydroxypropoxy)-4-(trans-4-propylcyclohexyl)benzene as a compound of the present invention obtained in Example 2 (15 parts by weight) with the liquid crystal composition (B) (85 parts by weight) has a nematic-clearing point of 68.1° C., a dielectric anisotropy value of +12.2 and a viscosity at 20° C. of 37.2 cp. When this liquid crystal composition (C) was filled in the above TN cell, the resulting liquid crystal cell exhibited a threshold voltage of 1.56 V and a saturation voltage of 2.19 V at 20° C.

What we claim is:

1. A 1-hydroxyalkoxy-4-(trans-4-alkylcyclohexyl)-benzene compound of the formula

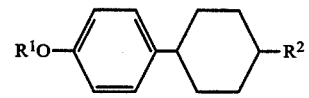

wherein $R^1$ represents a hydroxyalkyl group of 1 to 10 carbon atoms having a hydroxyl group at the end or an intermediate position thereof and $R^2$ represents an alkyl group of 1 to 10 carbon atoms.

2. A liquid crystal composition having at least two components at least one of which is a compound as defined in claim 1.

* * * * *